(12) United States Patent
Humble (10) Patent No.: US 9,787,075 B2
(45) Date of Patent: Oct. 10, 2017

(54) CABLE TRACK FOR SCANNING HEAD OF PAPER MACHINE OR OTHER SYSTEM

(71) Applicant: Honeywell ASCa Inc., Mississauga (CA)

(72) Inventor: Bradley Humble, Vancouver (CA)

(73) Assignee: Honeywell Limited, Mississauga (CA)

( * ) Notice: Subject to any disclaimer, the term of this patent is extended or adjusted under 35 U.S.C. 154(b) by 85 days.

(21) Appl. No.: 13/874,445

(22) Filed: Apr. 30, 2013

(65) Prior Publication Data
US 2014/0319288 A1    Oct. 30, 2014

(51) Int. Cl.
*A61B 6/00* (2006.01)
*H02G 11/00* (2006.01)
*B65G 17/20* (2006.01)

(52) U.S. Cl.
CPC .......... *H02G 11/006* (2013.01); *A61B 6/4464* (2013.01); *A61B 6/56* (2013.01); *B65G 17/20* (2013.01)

(58) Field of Classification Search
CPC ........ A61B 6/4464; A61B 6/56; B65G 17/20; F16M 11/42; F16M 11/425; F16M 13/027; F21V 21/34; F21W 2131/20; Y10S 362/804
USPC ............ 248/49, 58, 60, 61, 323, 317, 298.1; 211/162; 362/804, 249.09; 378/197
See application file for complete search history.

(56) References Cited

U.S. PATENT DOCUMENTS

| 4,658,577 | A |   | 4/1987 | Klein |
|---|---|---|---|---|
| 4,702,281 | A | * | 10/1987 | Moritz .......................... 138/120 |
| 5,025,115 | A | * | 6/1991 | Sayegh ................ H01B 7/0838 174/117 F |
| 5,377,892 | A |   | 1/1995 | Kimball |
| 5,664,957 | A | * | 9/1997 | Starr .............................. 439/207 |
| 5,759,350 | A |   | 6/1998 | Pyron et al. |
| 6,546,644 | B2 |   | 4/2003 | Poineau et al. |
| 7,310,935 | B2 | * | 12/2007 | Worms .......................... 59/78.1 |
| 7,388,154 | B2 | * | 6/2008 | Chen et al. ............... 174/117 F |
| 7,490,500 | B2 |   | 2/2009 | Hernandez, Jr. et al. |

(Continued)

FOREIGN PATENT DOCUMENTS

| DE | 20 2005 008668 U1 | 8/2005 |
|---|---|---|
| DE | 10 2012 100359 A1 | 7/2012 |

(Continued)

OTHER PUBLICATIONS

"Ribbon cable", www.wikipedia.org, Feb. 26, 2013, 4 pages.

(Continued)

*Primary Examiner* — Nkeisha Smith (57) ABSTRACT

An apparatus includes a cable track configured to be coupled to a moveable object and to be pushed and pulled by the movable object without buckling. The cable track is also configured to transport at least one signal or material to or from the moveable object. The cable track has a curved profile. A cross-section of the cable track showing a height, a width, and a thickness of the cable track can have a "(" shape. The cable track can be configured to be bent in order to create a "U" bend in the cable track, and the cable track can be configured to be pushed and pulled without buckling to change a location of the "U" bend along the cable track. The cable track can be configured to change shape repeatedly between a "J" shape and a "U" shape.

21 Claims, 7 Drawing Sheets

(56) References Cited

U.S. PATENT DOCUMENTS

| | | | |
|---|---|---|---|
| 7,520,473 B2* | 4/2009 | Karlinger | 248/49 |
| 7,784,259 B2* | 8/2010 | O'Rourke et al. | 59/78.1 |
| 7,819,034 B2 | 10/2010 | Jasinski | |
| 8,154,859 B2* | 4/2012 | Shahrokhi | 361/679.01 |
| 9,163,698 B2* | 10/2015 | Kaihotsu | F16G 13/16 |
| 2005/0011665 A1 | 1/2005 | Youngers et al. | |
| 2011/0157663 A1 | 6/2011 | Liu | |
| 2012/0187271 A1 | 7/2012 | Komiya | |
| 2012/0205498 A1* | 8/2012 | Komiya | 248/49 |
| 2012/0228437 A1* | 9/2012 | Tatsuta et al. | 248/49 |
| 2013/0075128 A1* | 3/2013 | Kaihotsu et al. | 174/68.3 |
| 2014/0042280 A1* | 2/2014 | Takeuchi et al. | 248/49 |
| 2014/0263866 A1* | 9/2014 | Hemmer | 248/58 |

FOREIGN PATENT DOCUMENTS

| | | |
|---|---|---|
| EP | 2 565 631 A2 | 3/2013 |
| WO | 2005/071284 A1 | 8/2005 |
| WO | 2012/132810 A1 | 10/2012 |

OTHER PUBLICATIONS

"High Performance Cable Solutions for the World of Semiconductors", LEONI Elocab Ltd., (No date), 10 pages.

"Flextrack, Self Supporting Flat Cables for the Automation and Robotics Industry", axon cable & interconnect, Nov. 2008, 2 pages.

"Core High Flex Flat Cable", W.L. Gore & Associates, Inc., Jul. 29, 2010, 2 pages.

"Core Trackless", W.L. Gore & Associates, Inc., Jul. 30, 2010, 2 pages.

Ronald E. Beselt, "Pneumatically-Expandable Cable Track for Scanning Head of Paper Machine or Other System", U.S. Appl. No. 13/874,430, filed Apr. 30, 2013.

Notification of Transmittal of the International Search Report and the Written Opinion of the International Searching Authority, or the Declaration dated Jul. 16, 2014 in connection with International Patent Application No. PCT/CA2014/000362.

Notification of Transmittal of the International Search Report and the Written Opinion of the International Searching Authority, or the Declaration dated Jul. 16, 2014 in connection with International Patent Application No. PCT/CA2014/000360.

European Patent Office, Application/Patent No. 14791777.7-1503 / 2992138, PCT/CA2014000362, "Supplementary European Search Report," dated Nov. 2, 2016, pp. 6, European Patent Office, Munich, Germany.

European Patent Office, Application/Patent No. 14792247.0-1903 / 2992580, PCT/CA2014000360, "Supplementary European Search Report," dated Oct. 31, 2016, pp. 4, European Patent Office, Munich, Germany.

\* cited by examiner

CABLE TRACK FOR SCANNING HEAD OF PAPER MACHINE OR OTHER SYSTEM

TECHNICAL FIELD

This disclosure relates generally to scanning systems. More specifically, this disclosure relates to a cable track for a scanning head of a paper machine or other system.

BACKGROUND

Webs or other sheets of material are used in a variety of industries and in a variety of ways. These materials can include paper, multi-layer paperboard, and other products manufactured or processed in long sheets. As a particular example, long sheets of paper can be manufactured and collected in reels.

It is often necessary or desirable to measure one or more properties of a sheet of material as the sheet is being manufactured or processed. Adjustments can then be made to the process in order to help ensure that the properties stay within desired ranges. Measurements are often taken using a scanning head that moves back and forth across the width of the sheet.

When running cables to a moving scanning head, a cable track is often used to secure the cables. While this allows the cables to be pulled in one direction, the cables typically cannot be pushed in the other direction without buckling. Also, multiple cables often must be bundled together to avoid tangling.

As a result, traditional cable track designs use plastic or metal snap links that enclose the cables and provide the stiffness required to push and pull the cable track as the scanning head moves back and forth. However, the use of snap links increases the cost and assembly time associated with the scanning head. Also, the natural frequency of the movement of the snap links can overlap with one or more of the scanning head's natural frequencies, causing undesirable vibrations. Another approach involves integrating all cables into a single flat bundle, but this still does not allow the cables to be both pulled and pushed over long distances.

SUMMARY

This disclosure provides a cable track for a scanning head of a paper machine or other system.

In a first embodiment, an apparatus includes a cable track configured to be coupled to a moveable object and to be pushed and pulled by the movable object without buckling. The cable track is also configured to transport at least one signal or material to or from the moveable object. The cable track has a curved profile.

In a second embodiment, a system includes a movable object configured to move back and forth and a cable track coupled to the moveable object. The cable track is configured to transport at least one signal or material to or from the moveable object. The movable object is configured to push and pull the cable track without buckling the cable track. The cable track has a curved profile.

In a third embodiment, a method includes coupling a cable track to a moveable object. The cable track is configured to transport at least one signal or material to or from the moveable object. The method also includes pushing and pulling the cable track with the moveable object without buckling the cable track. The cable track has a curved profile.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 7, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
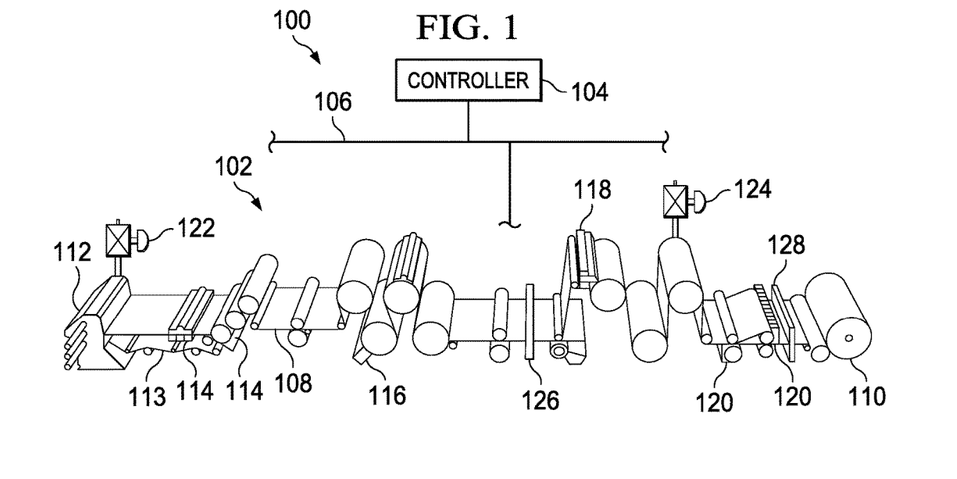
FIG. 1 illustrates an example sheet manufacturing or processing system according to this disclosure.

FIG. 1 illustrates an example sheet manufacturing or processing system 100 according to this disclosure. In this example, the system 100 includes a paper machine 102, a controller 104, and a network 106. The paper machine 102 includes various components used to produce a paper product, namely a paper sheet 108 that is collected at a reel 110. The controller 104 monitors and controls the operation of the paper machine 102, which may help to maintain or increase the quality of the paper sheet 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the sheet. The dilution water may be used to help ensure that the resulting paper sheet 108 has a more uniform basis weight across the sheet 108.

Arrays of drainage elements 114, such as vacuum boxes, remove as much water as possible to initiate the formation of the sheet 108. An array of steam actuators 116 produces hot steam that penetrates the paper sheet 108 and releases the latent heat of the steam into the paper sheet 108, thereby increasing the temperature of the paper sheet 108 in sections across the sheet. The increase in temperature may allow for easier removal of remaining water from the paper sheet 108. An array of rewet shower actuators 118 adds small droplets of water (which may be air atomized) onto the surface of the paper sheet 108. The array of rewet shower actuators 118 may be used to control the moisture profile of the paper sheet 108, reduce or prevent over-drying of the paper sheet 108, or correct any dry streaks in the paper sheet 108.

The paper sheet 108 is then often passed through a calendar having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper sheet 108. The arrays of induction heating actuators 120 may therefore be used to control the caliper (thickness) profile of the paper sheet 108. The nips of a calendar may also be equipped with other actuator arrays, such as arrays of air showers or steam showers, which may be used to control the gloss profile or smoothness profile of the paper sheet.

Two additional actuators 122-124 are shown in FIG. 1. A thick stock flow actuator 122 controls the consistency of incoming stock received at the headbox 112. A steam flow actuator 124 controls the amount of heat transferred to the paper sheet 108 from drying cylinders. The actuators 122-124 could, for example, represent valves controlling the flow of stock and steam, respectively. These actuators 122-124 may be used for controlling the dry weight and moisture of the paper sheet 108.

Additional components could be used to further process the paper sheet 108, such as a supercalender (for improving the paper sheet's thickness, smoothness, and gloss) or one or more coating stations (each applying a layer of content to a surface of the paper to improve the smoothness and printability of the paper sheet). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, the control system described below is not limited to use with systems for producing paper products and could be used with systems that process a paper product or with systems that produce or process other items or materials (such as multi-layer paperboard, cardboard, plastic, textiles, metal webs, or other or additional materials that are manufactured or processed as moving sheets).

In order to control the paper-making process, one or more properties of the paper sheet 108 may be continuously or repeatedly measured. The sheet properties can be measured at one or various stages in the manufacturing process. This information may then be used to adjust the paper machine 102, such as by adjusting various actuators within the paper machine 102. This may help to compensate for any variations of the sheet properties from desired targets, which may help to ensure the quality of the sheet 108.

As shown in FIG. 1, the paper machine 102 includes one or more scanners 126-128, each of which may include one or more sensors. Each scanner 126-128 is capable of measuring one or more characteristics of the paper sheet 108. For example, each scanner 126-128 could include sensors for measuring the caliper, anisotropy, basis weight, color, gloss, sheen, haze, surface features (such as roughness, topography, or orientation distributions of surface features), or any other or additional characteristics of the paper sheet 108.

Each scanner 126-128 includes any suitable structure or structures for measuring or detecting one or more characteristics of the paper sheet 108. For example, each scanner 126-128 could include one or more sets of sensors mounted on a scanning head that moves back and forth across the sheet 108. Note, however, that stationary sensors could also be used at one or more locations of the paper machine 102.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of the system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

As described in more detail below, one or more scanners 126-128 could include a cable track having multiple wires connected to a scanning head. Moreover, the cable track has a curved profile across its height, which increases the stiffness of the cable track when the cable track is being pushed. This allows the cable track to be pulled and pushed repeatedly as the scanning head moves back and forth without requiring the use of snap links or other support structures. This helps to avoid the problems associated with conventional cable track designs.

Although FIG. 1 illustrates one example of a sheet manufacturing or processing system 100, various changes may be made to FIG. 1. For example, other systems could be used to produce other paper or non-paper products. Also, while shown as including a single paper machine 102 with various components and a single controller 104, the system 100 could include any number of paper machines or other machinery having any suitable structure, and the system 100 could include any number of controllers. In addition, FIG. 1 illustrates one operational environment in which a cable track having a curved profile can be used. This functionality could be used in any other type of system, and that system need not manufacture or process moving webs or sheets.

Figure 2:
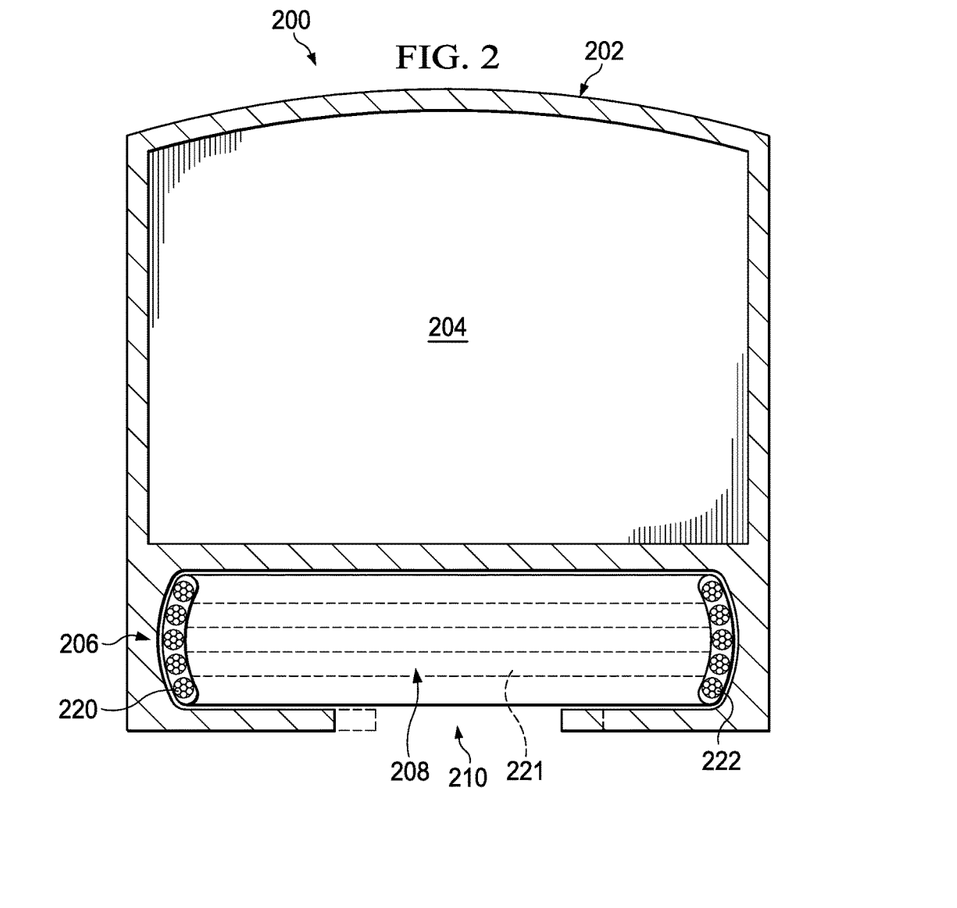
FIGS. 2 and 3 illustrate details of an example cable track used with a scanning head or other movable object according to this disclosure.
Figure 3:
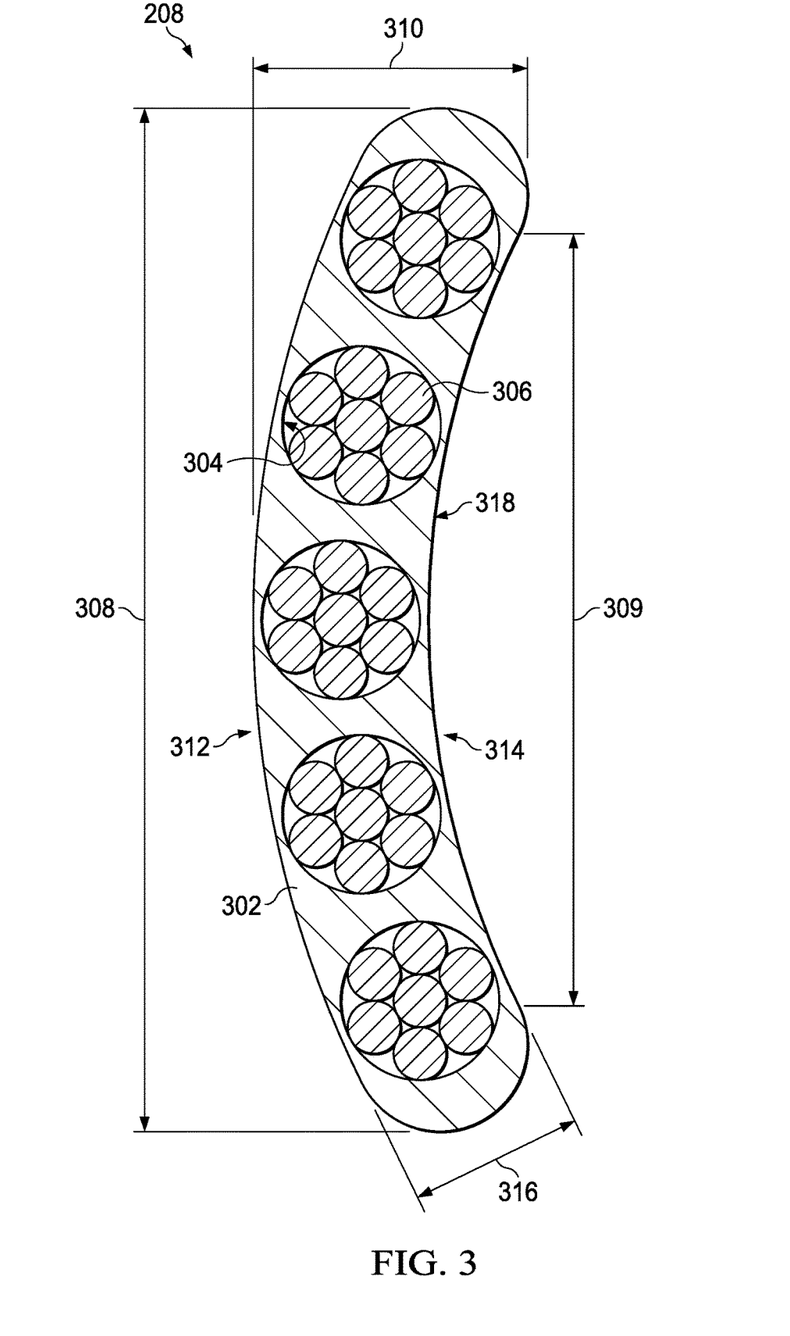

FIGS. 2 and 3 illustrate details of an example cable track used with a scanning head or other movable object according to this disclosure. FIG. 2 illustrates a cross-section of a structure 200 that supports the use of a cable track. The structure 200 itself could represent an elongated structure that extends any suitable distance, such as the distance across a paper machine 102. In particular embodiments, the structure 200 could form part of one or both scanners 126-128 in the system 100 of FIG. 1.

As shown in FIG. 2, the structure 200 includes a housing 202, which defines an opening 204. The housing 202 is designed to receive a beam or other support through the opening 204. The beam could, for example, represent a beam extending across the upper surface of the sheet 108 in the system 100. By placing the structure 200 onto this beam, the structure 200 is secured in place over the sheet 108.

The structure 200 also defines a second opening 206 below the opening 204. The second opening 206 represents an area where a cable track 208 can be inserted. The cable track 208 represents a structure containing, encasing, or otherwise supporting one or multiple wires for a scanning head or other movable object. A first portion 220 of the cable track 208 here extends along one side of the opening 206, the cable track 208 then loops back at a "U" bend 221, and a second portion 222 of the cable track 208 here extends along another side of the opening 206.

The housing 202 can be formed from any suitable material(s), such as one or more metals. The housing 202 can also be formed in any suitable manner, such as an extrusion process. In addition, the housing 202 can have any suitable size, shape, and dimensions. The opening 204 can have any suitable size and shape in the housing. The opening 206 can also have any suitable size and shape in the housing.

An opening 210 is provided along the bottom of the housing 202. The opening 210 allows the cable track 208 to exit the opening 206 and couple to a scanning head or other movable object. The movable object could be mounted to or under the housing 202. The opening 210 could have any suitable size and shape. Also, the opening 210 may or may not extend the entire length of the structure 200. In addition, while the opening 210 is shown here as being centered in the cross-section of the structure 200, the opening 210 could be offset to one side or the other in FIG. 2 (such as is shown by the dashed lines in FIG. 2).

As shown in this example, the cable track 208 has a curved profile. The cable track 208 is shown in greater detail in FIG. 3, which shows a cross-section of the cable track 208. As shown in FIG. 3, the cable track 208 includes a strength member 302. The strength member 302 generally gives the cable track 208 its curved profile. The strength member 302 also allows the cable track 208 to be deformed and then return substantially to its pre-deformed shape. The strength member 302 includes any suitable material(s) that can withstand repeated deformations, such as a metal.

The cable track 208 also includes one or more cable pods 304, each of which can include one or more wires or other cables 306. These cables 306 are used to provide signals to and receive signals from a scanning head. For example, the cables 306 could be used to supply electrical power and control commands or other data to the scanning head. The cables 306 could also be used to receive measurements and other data from the scanning head. The cable track 208 could include any number of cable pods 304, and each cable pod 304 could include any number of cables 306.

Note that the cable pods 304 and cables 306 are optional in the cable track 208, and the cable track 208 could include other mechanisms for providing signals or materials to or from a sensor head or other movable object. For instance, the cables 306 could be omitted, and the cable pods 304 could represent one or more hoses, tubes, or other structures configured to transport air, water, or other fluid(s). The phrase "cable track" therefore encompasses any suitable track that can transport at least one signal or material to or from a movable object.

The curved profile of the cable track 208 provides stiffness when the cable track 208 is pushed, but it also allows the cable track 208 to be deformed (such as in the "U" bend portion of the cable track 208). The cable track 208 here is said to be curved along its height. In this document, the "length" of a cable track is defined as the long dimension of the cable track (perpendicular to the image in FIG. 3). Also, the height 308 of an outer longer edge along an outer curve of a cable track is defined as the dimension from one shorter edge of the cable track to the opposing shorter edge of the cable track (up and down in FIG. 3). The height 309 of an inner longer edge along an inner curve of a cable track is defined as the dimension from one shorter edge of the cable track to the opposing shorter edge of the cable track (up and down in FIG. 3). The width 310 of a cable track is defined as the horizontal dimension from the center of the outer longer edge 312 of the cable track to the opposing extremity of the inner longer edge 314 of the cable track (left to right in FIG. 3). Finally, the thickness 316 is defined as the dimension from the outer longer edge 312 of the cable track to the inner longer edge 314 of the cable track. Since the cable track has a longer curved height and a smaller width, the cable track is said to have a "(" profile since this profile resembles a parenthesis. In addition, the term "profile" refers to a view of a cross-section of a cable track, where the cross section shows the height 308, height 309, width 310, and thickness 316 of the cable track. Note, however, that the use of the term "height" here does not limit a cable track to any particular orientation while in use. The profile also shows the cross-section of the cable track forming a closed loop 318.

Note that in FIG. 3, the cables 306 are embedded within the cable track 208. However, other designs of the cable track 208 could also be used. For example, one or more cables 306, tubes for carrying fluid, or other structures could be mounted to the outer surface(s) of the cable track 208. A combination of structures fully or partially embedded or contained within the cable track and structures mounted to the outer surface(s) of the cable track could also be used.

The cable track 208 could be fabricated in any suitable manner. For example, the cable track 208 could be fabricated using an extrusion process. The height, width, thickness, and curvature of the cable track 208 and the particular strength member(s) 302 used in the cable track 208 could be varied to obtain the desired flexibility and stiffness of the cable track 208 for a given application. Surface and wear features can also be added to the cable track 208. A wear surface could be placed along any portion of the cable track 208 that could wear against another structure.

Although FIGS. 2 and 3 illustrate details of one example cable track 208 used with a scanning head or other movable object, various changes may be made to FIGS. 2 and 3. For example, while shown as being used within the structure 200, the cable track 208 could be used with any other suitable device.

Figure 4:
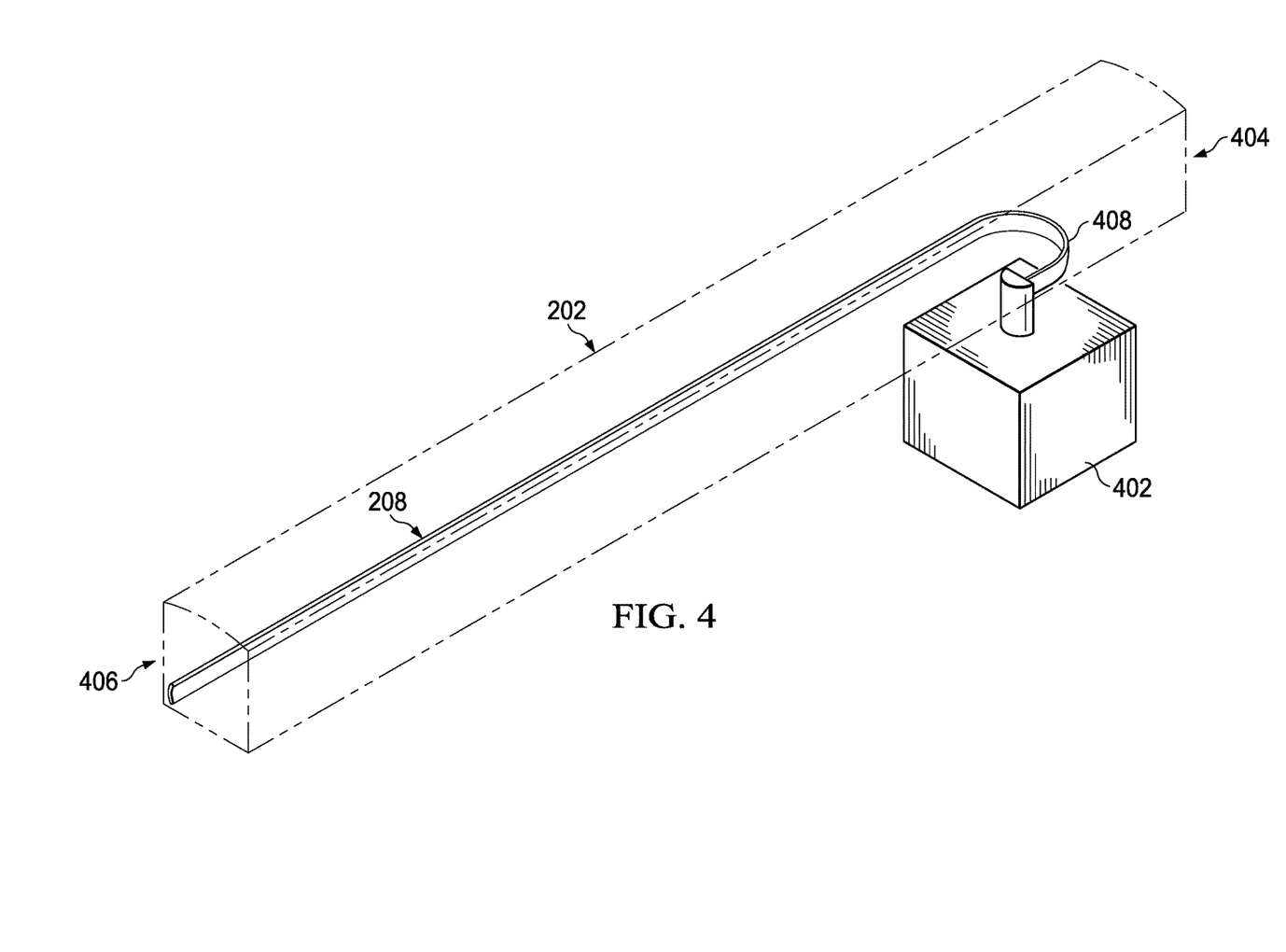
FIGS. 4 through 6 illustrate example operations of a cable track used with a scanning head or other movable object according to this disclosure.
Figure 5:
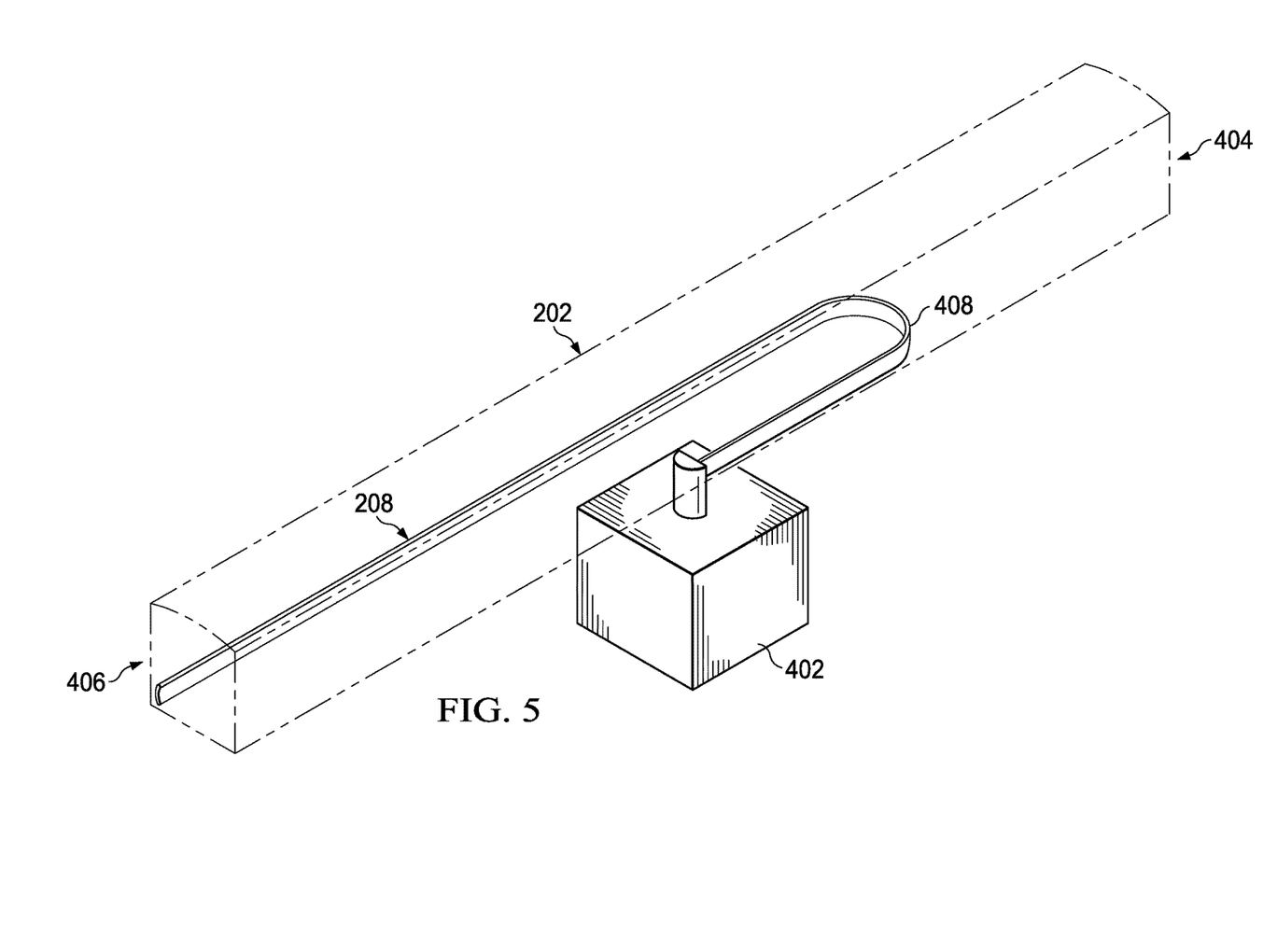
Figure 6:
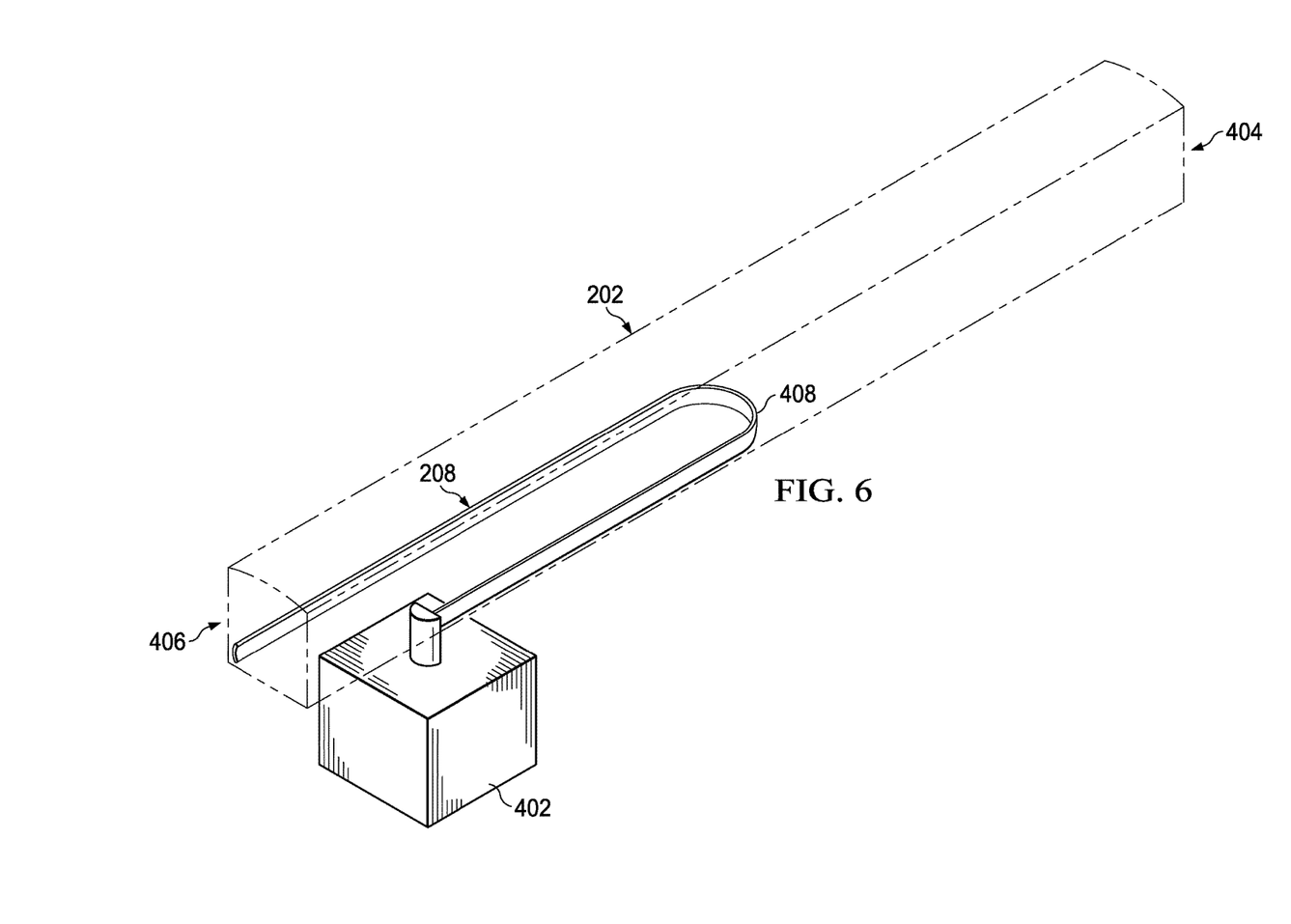

FIGS. 4 through 6 illustrate example operations of a cable track 208 used with a scanning head or other movable object according to this disclosure. In particular, FIGS. 4 through 6 illustrate a scanning head 402 moving along under the housing 202. Note that the scanning head 402 could be mounted on the housing 202 itself or under the housing 202.

In FIG. 4, the scanning head 402 is positioned near a first end 404 of the housing 202. One end of the cable track 208 can be secured to an object at or near a second end 406 of the housing 202. The other end of the cable track 208 can be secured to the scanning head 402. In this position, the cable track 208 has a "J" shape, meaning the cable track 208 extends along one side of the housing 202, makes a "U" bend 408, and extends a short way along the other side of the housing 202.

In FIG. 5, the scanning head 402 has moved approximately halfway along the housing 202. During this movement, the scanning head 402 pulls on the cable track 208. At this point, the cable track 208 has a shape somewhat between a "J" shape and a "U" shape. The cable track 208 still makes the "U" bend 408, but the "U" bend 408 is now in a different location of the cable track 208.

In FIG. 6, the scanning head 402 has moved near the second end 406 of the housing 202. Again, during this movement, the scanning head 402 pulls on the cable track 208. The cable track 208 is now substantially "U" shaped. Again, the cable track 208 still makes the "U" bend 408, but the "U" bend 408 is in a different location of the cable track 208.

The scanning head 402 then traverses back across the housing 202 towards the first end 404 of the housing 202. During this movement, the scanning head 402 pushes on the cable track 208. As a result, the cable track 208 can assume the configuration shown in FIG. 5 since the scanning head 402 is pushing the cable track 208. Eventually, the cable track 208 can assume the configuration shown in FIG. 4 when the scanning head 402 reaches the first end 404 of the housing 202. This process can repeat any number of times as the scanning head 402 moves back and forth.

As can be seen in FIGS. 4 through 6, the cable track 208 is able to be coupled to an object moving back and forth without requiring the use of snap links. This helps to eliminate the costs, delays, and undesirable vibrations associated with the use of snap links. Ordinarily, the lack of snap links would cause a conventional cable track to buckle when it is being pushed. The force required to buckle a column is proportional to the column's modulus of elasticity and moment of inertia and is inversely proportional to the square of the column's length. When used with respect to a cable track, this can be expressed as $F \propto EI/L^2$, where E represents the modulus of elasticity of the cable track, I represents the smaller of the two area moments of inertia of the cross section of the cable track, and L represents the length of the cable track. Stiffness is defined as the product of "E" and "I". Selecting an appropriate material for the cable track can help to increase the length "L" achievable before buckling occurs as it defines the "E" value. Increasing the "I" value can be achieved in a number of ways, such as by altering the size and shape of the cross section of the cable track. However, increasing the stiffness of the cable track, particularly in the direction of the "U" bend, increases the natural bend radius of the cable track, thus requiring a larger area for the cable track. It could also cause excessive stresses within the cable track and ultimately lead to failure. Using a cable track 208 with a suitable curved profile provides suitable stiffness to resist buckling while allowing the cable track 208 to flatten out around the "U" bend 408, reducing the bend radius and temporarily reducing the "I" value and the associated stresses within the strength member 302. The cable track 208 can return to its original curved profile on either side of the "U" bend 408.

Although FIGS. 4 through 6 illustrate example operations of a cable track 208 used with a scanning head or other movable object, various changes may be made to FIGS. 4 through 6. For example, the cable track 208 here is used in an orientation where the "U" and "J" shapes are generally horizontal within the housing 202. However, the cable track 208 is not limited to this particular orientation. The cable track 208 could be used in an orientation where the "U" and "J" shapes are generally vertical or in any other suitable orientation.

Figure 7:
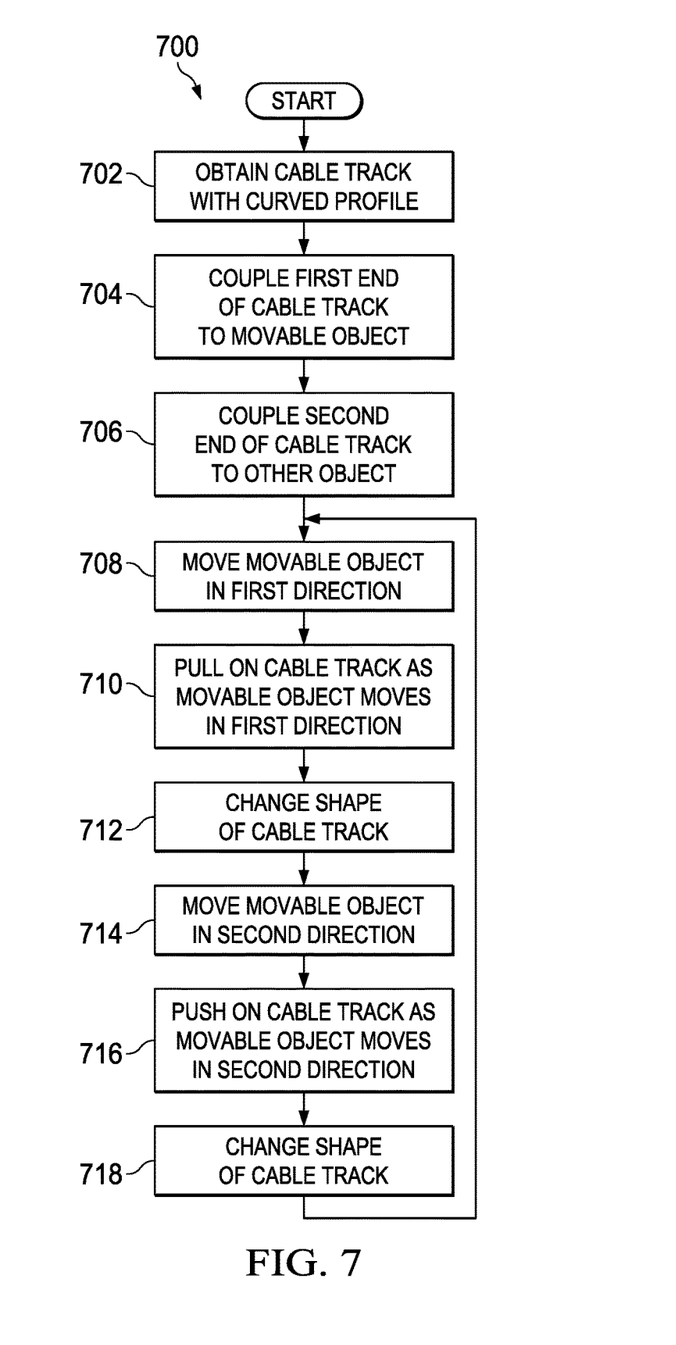
FIG. 7 illustrates an example method for using a cable track with a scanning head or other movable object according to this disclosure.

FIG. 7 illustrates an example method 700 for using a cable track with a scanning head or other movable object according to this disclosure. As shown in FIG. 7, a cable track with a curved profile is obtained at step 702. This could include, for example, obtaining a cable track 208 with the appropriate number(s) and type(s) of cables 306 for a desired application. The cable track 208 has a cross-section with a ")" profile.

A first end of the cable track is coupled to a movable object at step 704, and a second end of the cable track is coupled to another object at step 706. This could include, for example, coupling the cables 306 in the cable track 208 to a scanning head 402 or other movable object. This could also include coupling the cables 306 in the cable track 208 to another portion of a sheet-making or sheet-processing system.

The movable object is moved in a first direction at step 708. This could include, for example, moving the scanning head 402 in a first direction over a sheet 108. During this time, the movable object pulls on the cable track as the movable object moves in the first direction at step 710, which changes the shape of the cable track at step 712. This could include, for example, the scanning head 402 pulling on the cable track 208 to change the shape of the cable track 208 from a "J" shape to a "U" shape. This could also include the "U" bend 408 of the cable track 208 changing locations along the cable track 208.

The movable object is moved in a second direction at step 714. This could include, for example, moving the scanning head 402 in a second direction over the sheet 108. During this time, the movable object pushes on the cable track as the movable object moves in the second direction at step 716, which changes the shape of the cable track at step 718. This could include, for example, the scanning head 402 pushing on the cable track 208 to change the shape of the cable track 208 from a "U" shape to a "J" shape. This could also include the "U" bend 408 of the cable track 208 changing locations along the cable track 208.

Steps 708-718 can be repeated any number of times as the movable object moves back and forth repeatedly. In a paper machine 102 or other sheet-making or sheet-processing system, the scanning head 402 could move back and forth many thousands of times, possibly even hundreds of thousands or millions of times during its operational lifetime.

Although FIG. 7 illustrates one example of a method 700 for using a cable track with a scanning head or other movable object, various changes may be made to FIG. 7. For example, while shown as a series of steps, various steps in FIG. 7 could overlap, occur in parallel, occur in a different order, or occur any number of times. As a particular example, steps 708-712 could all occur generally at the same time, and steps 714-718 could all occur generally at the same time.

Figure 8:
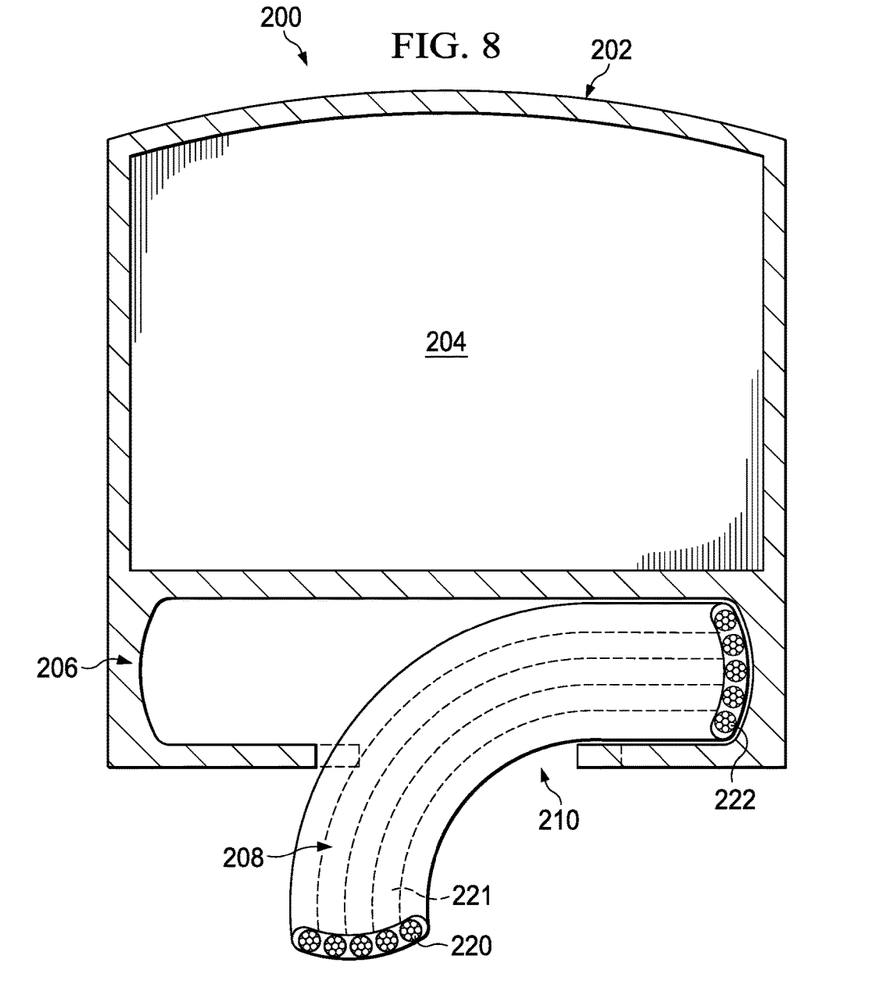
FIG. 8 illustrates details of an example cable track used with a scanning head or other movable object according to this disclosure.

FIG. 8 illustrates details of an example cable track used with a scanning head or other movable object according to this disclosure. As shown in FIG. 8, an opening 210 is provided along the bottom of the housing 202. The opening 210 allows the cable track 208 to exit the opening 206.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
    a housing comprising first, second, and third openings, the first opening configured to be secured to a support structure, and
    a cable track having a cross-section that forms a closed loop, the cable track configured to be coupled to a scanning head and to be pushed and pulled by the scanning head without buckling,
    wherein the cable track includes a first portion of the cable track extending along a first side of the second opening and a second portion of the cable track extending along a second side of the second opening,
    wherein the third opening allows the cable track to exit the second opening through the third opening,
    wherein the cable track is configured to transport at least one signal or material to or from the scanning head within the closed loop,
    wherein the cable track comprises a curved profile with an outer longer edge and an inner longer edge, and
    wherein a height of the cable track along the outer longer edge is greater than a height of the cable track along the inner longer edge.

2. The apparatus of claim 1, wherein the cross-section of the cable track has a "(" shape.

3. The apparatus of claim 1, wherein the cable track comprises:
    a strength member; and
    at least one of: one or more cables, one or more hoses, and one or more tubes fully within, partially within, or coupled to the strength member.

4. The apparatus of claim 1, wherein the cable track comprises:
    multiple cable pods, each cable pod comprising one or more cables.

5. The apparatus of claim 1, wherein:
    the cable track is configured to be bent in order to create a "U" bend in the cable track; and
    the cable track is configured to be pushed and pulled without buckling to change a location of the "U" bend along the cable track.

6. The apparatus of claim 1, wherein the cable track is configured to change shape repeatedly between a "J" shape and a "U" shape.

7. A system comprising:
    a scanning head configured to move back and forth;
    a housing comprising first, second, and third openings, the first opening configured to be secured to a support structure; and
    a cable track having a cross-section that forms a closed loop, the cable track coupled to the scanning head,
    wherein the cable track includes a first portion of the cable track extending along a first side of the second opening and a second portion of the cable track extending along a second side of the second opening,
    wherein the third opening allows the cable track to exit the second opening through the third opening,
    wherein the cable track comprises a curved profile with an outer longer edge and an inner longer edge, a height of the cable track along the outer longer edge greater than a height of the cable track along the inner longer edge,
    wherein the cable track is configured to transport at least one signal or material to or from the scanning head within the closed loop, and
    wherein the scanning head is configured to push and pull the cable track without buckling the cable track.

8. The system of claim 7, wherein the cross-section of the cable track has a "(" shape.

9. The system of claim 7, wherein the cable track comprises:
    a strength member; and
    at least one of: one or more cables, one or more hoses, and one or more tubes fully within, partially within, or coupled to the strength member.

10. The system of claim 7, wherein the cable track comprises:
    multiple cable pods, each cable pod comprising one or more cables.

11. The system of claim 7, wherein:
    the cable track is configured to be bent in order to create a "U" bend in the cable track; and
    the cable track is configured to be pushed and pulled without buckling to change a location of the "U" bend along the cable track.

12. The system of claim 7, wherein the cable track is configured to change shape repeatedly between a "J" shape and a "U" shape.

13. The system of claim 7, wherein the scanning head is configured to measure one or more characteristics of a sheet of material.

14. A method comprising:
    placing a cable track within a housing comprising first, second, and third openings by:
        extending a first portion of the cable track along a first side of the second opening, and
        extending a second portion of the cable track along a second side of the second opening, wherein the first opening is secured to a support structure;
    coupling the cable track to a scanning head, the cable track having a cross-section that forms a closed loop, wherein the cable track is configured to transport at least one signal or material to or from the scanning head within the closed loop, wherein the third opening allows the cable track to exit the second opening through the third opening; and
    pushing and pulling the cable track with the scanning head without buckling the cable track;
    wherein the cable track comprises a curved profile with an outer longer edge and an inner longer edge, a height of the cable track along the outer longer edge is greater than a height of the cable track along the inner longer edge.

15. The method of claim 14, wherein the cross-section of the cable track has a "(" shape.

16. The method of claim 14, wherein:
    the cable track is bent in order to create a "U" bend in the cable track; and
    the cable track is pushed and pulled without buckling to change a location of the "U" bend along the cable track.

17. The method of claim 14, wherein the cable track changes shape repeatedly between a "J" shape and a "U" shape.

18. The method of claim 14, wherein the method further comprises measuring one or more characteristics of a sheet of material using the scanning head.

19. The apparatus of claim 1, wherein a curvature of the outer longer edge across the height of the cable track substantially equals a curvature of the inner longer edge across the height of the cable track.

20. The apparatus of claim 1, wherein the third opening is offset in a bottom surface of the apparatus.

21. The apparatus of claim 1, wherein the third opening is centered in a bottom surface of the apparatus.

\* \* \* \* \*